United States Patent [19]

LaBove

[11] Patent Number: 4,863,454

[45] Date of Patent: Sep. 5, 1989

[54] DUAL BAG INTRAVENOUS PREPARATION SYSTEM

[76] Inventor: Larry D. LaBove, 4545 Kingwood Dr., #706, Kingwood, Tex. 77345

[21] Appl. No.: 118,189

[22] Filed: Nov. 6, 1987

Related U.S. Application Data

[63] Continuation-in-part of Ser. No. 109,577, Oct. 16, 1987.

[51] Int. Cl.[4] .............. A61B 19/00

[52] U.S. Cl. .............. 604/416; 60/414; 60/410

[58] Field of Search .............. 604/56, 80, 81, 82, 604/85, 86, 89, 92, 410, 416, 1, 414

[56] References Cited

U.S. PATENT DOCUMENTS

| | | | |
|---|---|---|---|
| 1,157,439 | 10/1915 | Starr | 604/80 |
| 3,469,578 | 9/1969 | Bierman | 128/214 |
| 3,486,539 | 12/1969 | Jacuzzi | 141/329 |
| 3,993,069 | 11/1976 | Buckles et al. | 128/214 |
| 4,201,207 | 5/1980 | Buckles et al. | 128/214 |
| 4,250,879 | 2/1981 | Muetterties | 604/81 |
| 4,258,723 | 3/1981 | McCue et al. | 604/82 |
| 4,318,400 | 3/1982 | Peery et al. | 128/214 |
| 4,336,802 | 6/1982 | Stone et al. | 604/414 |
| 4,507,114 | 3/1985 | Bohman et al. | 206/219 X |
| 4,623,334 | 11/1986 | Riddell | 604/85 |

OTHER PUBLICATIONS

Abbott Nutrimix Dual-Chamber Plastic Container Brochure, dated May, '85.

Burroughs Wellcome Co. "Add-Vantage" 1985.

Travenol ® Infusor-2 Catalogs (one dated 1984).

Abbott Laboratories—Instruction Sheet 1985.

American McGaw Hospital Catalog and Price List, p. 28.

*Primary Examiner*—Allen M. Ostrager

*Attorney, Agent, or Firm*—Vaden, Eickenroht, Thompson & Boulware

[57] ABSTRACT

A method and apparatus for preparation and delivery of an intravenous therapeutic agent with features that minimize the possibility of contamination, exposure and improper dosage level of the drug. One container is pre-filled with a diluent. Another container is pre-filled with a dry form drug. The containers are joined with a flow connector in between. When the drug is prescribed, the diluent is allowed to flow into the drug container for mixing and is administered.

10 Claims, 4 Drawing Sheets

DUAL BAG INTRAVENOUS PREPARATION SYSTEM

This application is a continuation-in-part of Ser. No. 109,577 filed Oct. 16, 1987 for "Intravenous therapeutic Agent Preparation and Administration System" pending.

BACKGROUND AND SUMMARY OF THE INVENTION

The preparation and delivery of intravenous drugs must be done using aseptic techniques and with careful attention to proper dosage. Particularly, cancer patients with depressed immune systems from treatments, have a greater susceptibility of infection. Therapeutic agents often are manufactured in lyophilized or powdered form for stability or ease in handling and shipping. The dry form of the therapeutic agent is admixed with the appropriate volume of sterile diluent to provide a uniform mixture and reconstitute the drug.

A typical procedure for reconstitution of an intravenous drug includes several steps. A drug in dry form typically is received in a vial. A syringe is used to withdraw the appropriate volume of sterile diluent from a diluent container and inject the diluent solution into the drug vial. The drug vial and diluent vial typically have rubber stoppers and the needle of the syringe is injected in and out of the stoppers.

The drug and diluent are admixed in the drug vial. Often the dry form drug is difficult to mix into solution in the diluent. Some drugs need to be reconstituted in a liquid prior to administration. Other drugs have a shorter stability period and once mixed with a liquid must be frozen to maintain efficacy for a prolonged period of time. For intravenous usage, the drugs must be in solution and placed into an intravenous delivery system. The appropriate dosage may require additional dilutions or other manipulation including adding other drugs to the mixture.

There are a variety of intravenous delivery systems. A common device is a flexible bag or vial with a fill portal and intravenous delivery tube for the patient. Intravenous infusors have been developed which have a tube with an expanding latex bladder inside the vial which has an injection port on one end of the bladder, accessible from outside the vial, to add the drug and an intravenous delivery tube on the other end of the bladder, extending outside the vial.

The multiple steps and manipulations of intravenous drug preparation and delivery equipment increase the chance for a failure in aseptic technique. The multiple transfer of a dosage increases the chance for waste of the drug or improper dosage due to potential loss during transfer.

Also, there is a risk of exposure to certain drug products such as oncolytic chemotherapeutic agents which are mutagenic or otherwise harmful to the health care worker handling the agent. In particular, when injecting a drug vial under pressure while withdrawing the syringe, there can be an aerosol effect which causes an emission of a spray from the rubber stoppered vial if the pressure in the vial is not released. The exposure of health care workers to oncolytic agents has been reported in Anderson et al., "Risk of Handling Injectable Antineoplastic Agents," *Am. J. Hosp. Pharm.*, Vol. 39, pp. 1881–1887 (1982).

Some medications are sold premixed with various diluents. The premixing can affect the stability of some drugs and others must be frozen to maintain therapeutic efficacy. Other systems include a sealed vial which is received into a neck on a bag filled with fluid. A cap is broken off inside the bag to release the drug out of the vial. This system has several steps of preparation and requires properly sized vials and other equipment to perform the mixing.

Another system includes an amount of lyophilized or dry drug in a compartment of a container and a diluent in another compartment separated by an impervious rubber stopper. When ready for use the rubber stopper separating the diluent and the drug is dislodged and the components are mixed. The mixture must be withdrawn from the container and placed in an administration system.

In another system a one piece bag with upper and lower chambers is divided by a pinch clamp which is released to mix the two premeasured liquid components contained in the chambers. The liquids from the two chambers are manipulated to achieve mixing and fall by gravity to the lower chamber when the bag is held upright.

The apparatus and method of the present invention uses two containers, one holding a diluent and the other containing an adequate amount of the dry therapeutic agent. The containers are manufactured with the constituent components and either joined during fabrication or later. The connection joining the two containers has a flow control to selectively open and close communication between the two containers.

Typically the apparatus is used with the first container containing the diluent connected above the second container with the dry form therapeutic agent to be put into solution for intravenous administration. The connector with the flow control is opened so that diluent goes into the second container by gravity flow. After the diluent is added, the mixing occurs preferably with the flow control closed on the connector.

In one embodiment, the two containers are flexible bags that are permanently joined during manufacture with a dosage of drug in the second container and the appropriate volume of diluent in the first container. The bags are joined with a sealed tubular connector with a flow control device such as a two-way stop cock in between. In another embodiment, the two bags can be manufactured without joinder, but have a connection means which can be maintained sterile prior to using.

The method of this invention includes the fabrication of two containers, the first which holds diluent and the second that contains a dry form therapeutic agent. The two containers are joined. At the connection, the flow from the first container into the second container can be controlled. When the drug is intended to be administered, the mixing occurs. The mixture can be dispensed or administered intravenously from one of the containers. The drug is freshly reconstituted at the time of administration.

This apparatus and method is designed to provide a flexible and simple way to handle therapeutic agents. The system reduces the chance for loss of sterility, exposure to harmful agents and improper dosage. The system is also efficient for use by health care professionals since no measuring or transfer of diluent or drug is necessary in the single dosage application. In a multiple dosage system of this invention the handling and transfer are minimal.

The dual container system of the present invention is flexible because the diluent and therapeutic agent can be handled separately during the manufacturing process. If one of the components is heat labile and cannot withstand certain sterilization procedures such as autoclaving, the sterilization procedure can be different for each container and its contents prior to connection. During manufacturing, there is flexibility depending on a need for which and how much diluent or drug is chosen to be placed in the containers. This procedure can enhance the ability to fill specific orders matching the drug and the amount and type of diluent.

DESCRIPTION OF THE PREFERRED EMBODIMENTS AND METHODS

Figure 1:
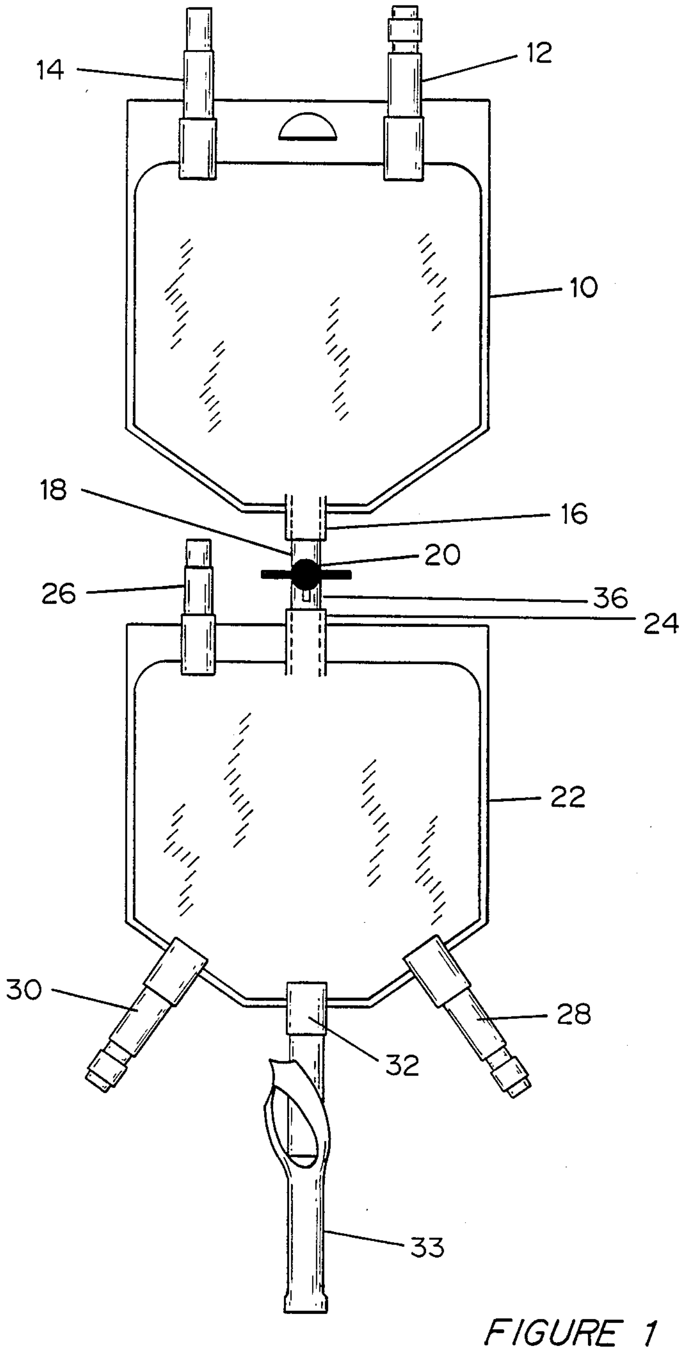
FIG. 1 is a frontal perspective view of the system for intravenous administration.

The preferred method and apparatus to practice the method including some alternatives are shown in the drawings. The containers are preferably flexible bags of a plastic capable of maintaining a sterile environment. Other materials compatible with sterility requirements can be used.

FIG. 1 shows a first container 10 which is fabricated to be filled with a diluent which may be introduced through fill portal 14 which is a tubular member appended to container 10 and communicates to the interior of container 10. Once the diluent is transferred in a sterile manner to container 10 portal 14 is sealed. Additional tubular additive portal 12 is appended and communicates with the interior of container 10. Container 10 has a tubular discharge portal 16 which is on the opposite end of portals 12 and 14 on container 10. Discharge portal 16 also communicates with the interior of container 10.

As shown in FIG. 1, a tubular connector 18 attaches at one end to discharge portal 16 and has a stop cock assembly 20 disposed in about the center of the connector 18. Connector 18 is attached on its opposite end to entry portal 24, a tubular member appended to and communicating with the interior of second container 22. The stop cock is shown in closed position in FIG. 1.

Container 22 is shown with a tubular fill portal 26 communicating with the interior of container 22 which can be used to introduce the dry form drug or therapeutic agent into second container 22. Fill portal 26 is sealed after use. Additional tubular additive portals 28 and 30 are appended to container 22 to be used if desired to add other constituents other than the various diluent and therapeutic agent. The fill portals on containers 10 and 22 are sealed. Entry through the additive portals is generally through injection diaphragms (not shown). The additive is introduced using a needle to pierce the diaphragm which is attached to a syringe containing the additive.

Container 22 has an intravenous fluid administration portal 32 appended and communicating with the interior of container 22. The administration portal 32 is on the opposite end of second container 22 from the entry portal 24. At the time desired to make up the intravenous mixture the stop cock 20 is rotated to the open position and the diluent in container 10 flows into container 22 through connector 18. The stop cock is closed and admixing is performed. After mixing, an intravenous delivery system is connected to administration portal 32. The administration portal 32 is kept sterile with a packaging or wrap 33 shown on FIG. 1 which is removed prior to use.

Figure 4:
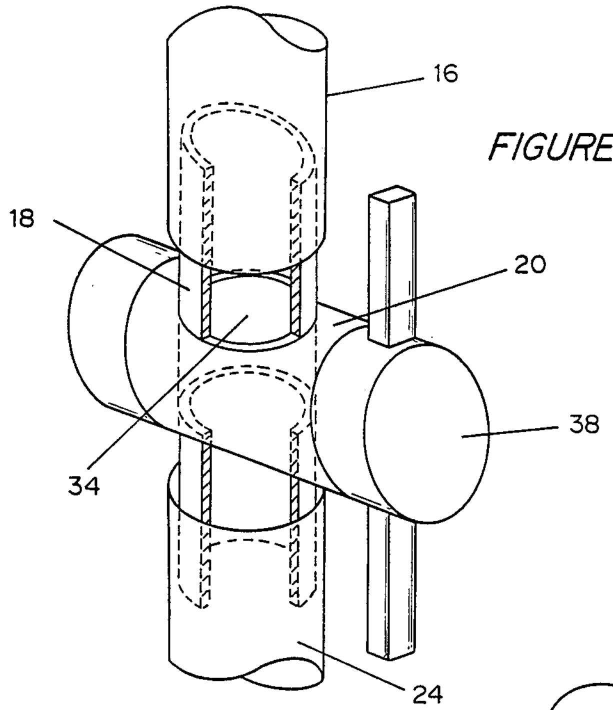
FIG. 4 is a partial cutaway view of the flow control in open position.
Figure 5:
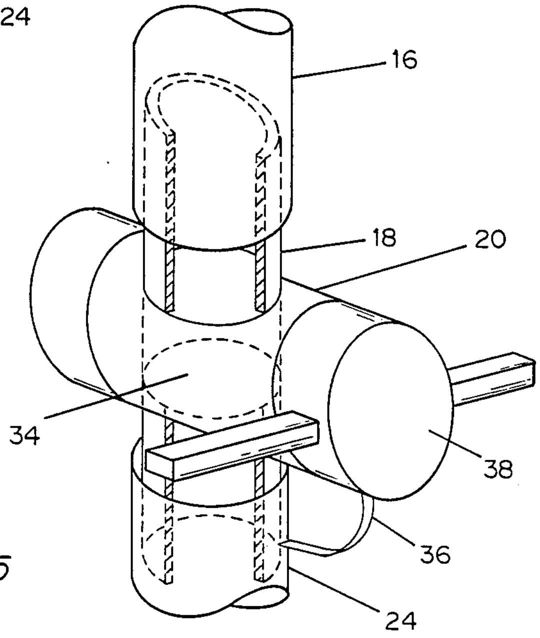
FIG. 5 is a partial cutaway view of the flow control in closed position.

FIGS. 4 and 5 show a detail of the stop cock 20 in open and closed positions respectively. As noted, the stop cock is centrally located on tubular connector 18 which attaches to discharge portal 16 and entry portal 24. During manufacturing, connector 18 is sealed to the portals to prevent any leakage.

FIG. 5 shows the closed position of stop cock 20 with orifice 34 of the stop cock rotated so that it is not in communication with the internal diameter of tubular connector 18. A safety feature shown in the drawings is safety attachment 36 which is a short length of plastic attached from the turning knob 38 of the stop cock to the outside of connector 18. The stop cock is held in the closed position shown in FIG. 5 with the aid of the safety attachment 36 to prevent realignment of the orifice 34 prior to use. With some pressure turning the stop cock knob, the safety attachment 36 is broken to allow rotation of the stop cock to the open position shown in FIG. 4 with orifice 34 in communication with the discharge portal 16 through connector 18 and with entry portal 24 also through connector 18. The diluent from the first container flows by gravity to the second container holding the dry form drug.

Figure 2:
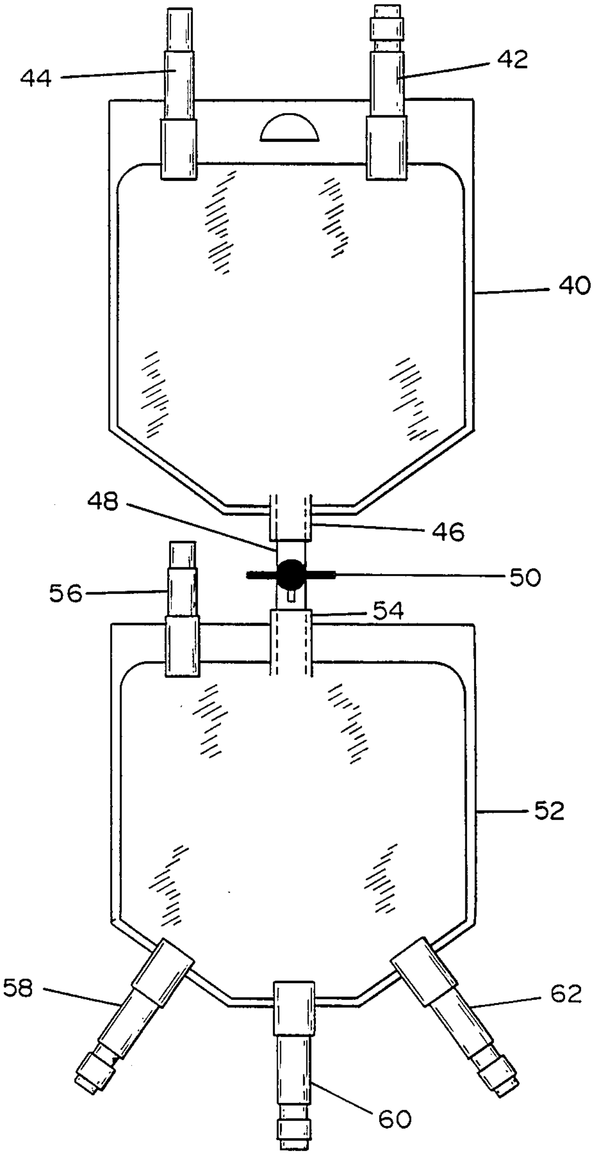
FIG. 2 is a frontal perspective view of an alternative embodiment for preparation of the solution.

FIG. 2 is an alternative embodiment which can be used in the method of preparation of multiple dosages of a therapeutic agent with a diluent. The components of the system are essentially identical with a first container 40 with diluent which may be added through fill portal 44. First container 40 has an additional additive portal 42 and discharge portal 46.

A connector tube 48 which is part of stop cock assembly 50 is attached on one end to the discharge portal 46 and has a stop cock 50 disposed in the center of the connector. Stop cock 50 is illustrated in FIGS. 4 and 5 and its operation is the same as discussed for the embodiment in FIG. 1.

In FIG. 2, second container 52 has an entry portal 54 which is attached to the end of connector 48 opposite to the discharge portal 46. A tubular fill portal 56 is appended to the top of container 52 and is provided for entry of the therapeutic agent as desired. On the bottom of container 52 three supplemental ports 58, 60 and 62 are shown. The ports 58, 60 and 62 can be used for adding constituents or discharge of the mixture to another container or delivery system as needed.

The embodiment of FIG. 2 operates in the same manner as discussed for FIG. 1 above with the exception that there is no intravenous portal present so that delivery to the patient cannot be achieved directly from container 52 without the addition of devices necessary to attach to an intravenous set.

Figure 3:
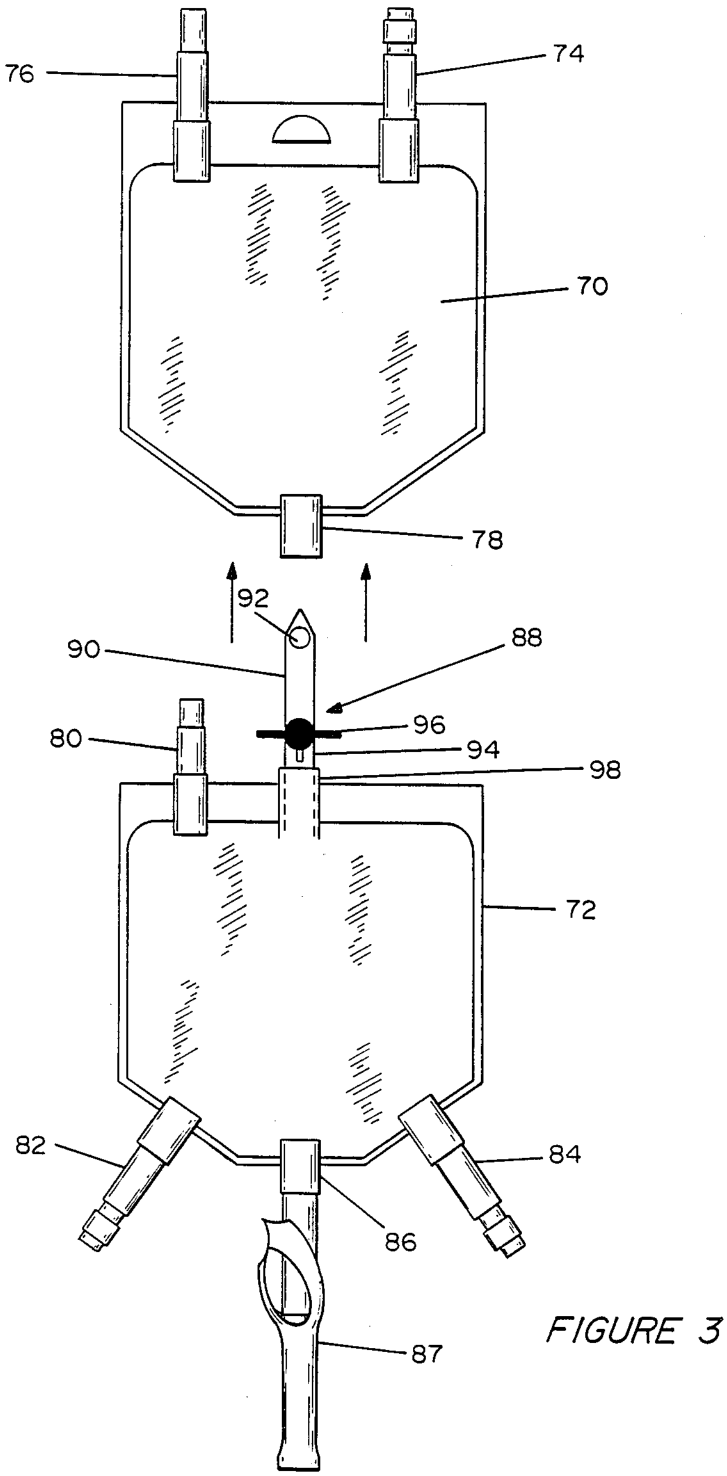
FIG. 3 is a frontal perspective view of a dual bag prior to connection.

FIG. 3 represents another embodiment of the system, the method of the invention is essentially the same. In this embodiment, the first container 70 and second container 72 are manufactured separately and are not joined until the time to mix the dry therapeutic agent and the diluent or can be joined by the manufacturer after each bag is aseptically filled with the appropriate component.

As in prior embodiments, container 70 is similarly provided with a fill portal 76, additional additive portal 74 and discharge portal 78 which are all sealed after the addition of diluent to container 70.

The second container 72 is provided with a fill portal 80 on the top of the container 72 through which the therapeutic agent may be added, and two additional additive portals 82 and 84 on the opposite end of container 72 along with an intravenous administration portal 86 which has a sterile wrapper 87. At the top of the container 72 is a stop cock assembly 88. In this embodiment of FIG. 3, the stop cock assembly 88 has an injection spike 90 with a lumen 92 through the center. The injection spike is made of a rigid material with a tapered, pointed end as shown. The injection spike 90 is firmly inserted through a diaphragm in discharge portal 78 when the dual bag system is ready for use.

The opposite end of spike 90 is a tubular member 94 of the stop cock assembly with a stop cock knob 96 disposed in the member 94 in a manner as described in other embodiments for the stop cock and tubular connection. The end of the member 94 opposite to that attached to the spike is attached to an entry portal 98 which is a tubular member communicating with the interior of container 72.

Container 72, with insertion assembly, is manufactured separately with the dry therapeutic agent contained therein. When used, a container of diluent is selected to mix with the chosen containerized drug. The spike 90 and the discharge portal 78 are wrapped or kept aseptic prior to use. The spike 90 is firmly inserted through the seal of discharge port 78 on container 70. The stop cock 96 is rotated to allow the diluent to flow into container 72 for mixing, and afterwards, for administration to the patient.

Container 72 may be modified as shown in FIG. 2 for use as a dispenser of multiple dosages with an intravenous portal. The embodiment of FIG. 3 allows for flexibility. The diluent and drug are not pre-joined prior to shipment so that varying combinations of diluent and dosage are available at the time of prescribing the drug.

The method practiced by the system includes fabricating a container, preferably a flexible bag, of diluent and also fabricating a similar container of a therapeutic agent with a measured amount sealed in the bags. The bags are joined together either during the manufacturing process or later. The diluent is allowed to flow into the container with the drug using a flow control device in the connection between the bags such as the stop cock. Once the diluent is completely drained into the bag containing the drug the stop cock is closed and the mixing occurs.

All the manipulation occurs without the health care worker being exposed to the drug. The solution is ready for dispensing or administration to the patient. The dosage is maintained in a controlled system so there is no loss or improper dilution.

What is claimed is:

1. An intravenous preparation and administration system comprising a first attachable container;

a sealable fill portal appended to said first attachable container communication to the interior of said first container;

a sealable discharge portal appended to said first attachable container communicating to the interior of said first attachable container;

a second attachable container;

a sealable fill portal appended to said second attachable container communicating to the interior of said second attachable container;

an intravenous fluid administration portal appended to said second attachable container communicating to the interior of said second attachable container;

a connector attached between said discharge portal of said first attachable container and the interior of said second attachable container; and a flow control actuator on said connector to selectively open and close the communication between said first attachable container when its discharge portal is not sealed and said second attachable container when its full portal is not sealed.

2. An intravenous preparation and administration system of claim 1 including at least one additional sealable additive portal appended to said first attachable container communicating with the interior.

3. An intravenous preparation and administration system of claim 1 including at least one additional sealable additive portal appended to said second attachable container communicating with the interior.

4. An intravenous preparation and administration system of claim 1 in which said first and second attachable containers are of flexible material.

5. An intravenous preparation and administration system of claim 1 wherein said conductor has a means for insertion into said sealable discharge portal on said first attachable container.

6. An intravenous preparation and administration system comprising a first attachable container;

a sealable fill portal appended to said first attachable container communicating to the interior of said first attachable container;

a sealable discharge portal appended to said first attachable container communicating to the interior of said first attachable container;

a second attachable container;

a sealable fill portal appended to said second attachable container communicating to the interior of said second attachable container;

a sealable discharge port appended to said second attachable container communicating with the interior of said second attachable container, a connector between said discharge portal of said first attachable container and the interior of said second attachable container; and a flow control actuator on said connector to selectively open and close the communication between said first attachable container when its discharge portal is not sealed and said second attachable container when its fill portal is not sealed.

7. An intravenous preparation and administration system of claim 6 including at least one additional sealable additive portal appended to said first attachable container.

8. An intravenous preparation and administration system of claim 6 including at least one additional sealable additive portal appended to said second attachable container.

9. An intravenous preparation and administration system of claim 6 in which said first and second attachable containers are of flexible material.

10. An intravenous preparation and administration system of claim 6 wherein said container has a means for insertion into said sealable discharge portal on said first attachable container.

* * * * *